US010905604B2

(12) United States Patent
Michiels et al.

(10) Patent No.: US 10,905,604 B2
(45) Date of Patent: *Feb. 2, 2021

(54) UNITARY ABSORBENT STRUCTURES COMPRISING AN ABSORBENT CORE AND/OR AN ACQUISITION AND DISPERSION LAYER FOR ABSORBENT ARTICLES

(71) Applicant: LIBELTEX, Meulebeke (BE)

(72) Inventors: Dany Michiels, Haalert (BE); Tanika Degrande, Inqelmunster (BE); Sara Vanwalleghem, Meulebeke (BE)

(73) Assignee: Libeltex, Meulebeke (BE)

( * ) Notice: Subject to any disclaimer, the term of this patent is extended or adjusted under 35 U.S.C. 154(b) by 954 days.

This patent is subject to a terminal disclaimer.

(21) Appl. No.: 14/394,231

(22) PCT Filed: Apr. 15, 2013

(86) PCT No.: PCT/EP2013/057849
§ 371 (c)(1),
(2) Date: Oct. 13, 2014

(87) PCT Pub. No.: WO2013/153235
PCT Pub. Date: Oct. 17, 2013

(65) Prior Publication Data
US 2015/0065974 A1    Mar. 5, 2015

(30) Foreign Application Priority Data
Apr. 13, 2012  (WO) .................. PCT/EP2012/056859

(51) Int. Cl.
*A61F 13/15*  (2006.01)
*A61F 13/20*  (2006.01)
(Continued)

(52) U.S. Cl.
CPC ........ *A61F 13/535* (2013.01); *A61F 13/1565* (2013.01); *A61F 13/15642* (2013.01);
(Continued)

(58) Field of Classification Search
CPC ............ A61F 13/53708; A61F 13/5376; A61F 2013/530576; A61F 2013/5307;
(Continued)

(56) References Cited

U.S. PATENT DOCUMENTS 4,232,674 A    11/1980  Melican
4,699,823 A *  10/1987  Kellenberger ........ A61F 13/534
                                                        428/212

(Continued)

FOREIGN PATENT DOCUMENTS

DE    WO 2000041882 A1    7/2000
EP            1870067 A1   12/2007
(Continued)

OTHER PUBLICATIONS

International Search Report within the European Patent Office, completed May 13, 2013 for International Patent Application No. PCT/EP2013/057849.

(Continued)

*Primary Examiner* — Michele M Kidwell
(74) *Attorney, Agent, or Firm* — Leydig, Voit & Mayer Ltd.; Gerald T. Gray

(57) ABSTRACT

The present invention relates to a unitary absorbent structure and method thereof wherein said unitary absorbent structure comprises an absorbent core (5) and/or an acquisition and dispersion layers (2) (3) and comprising at least one nonwoven fibrous substrate layer (23) having a void volume suitable to be penetrated by super absorbent particles. The super absorbent particles are dispersed in the substrate layer (23) according to a size distribution gradient by vacuum (8')

(Continued)

and vibration along the depth direction or z-direction of said absorbent core (5) and/or acquisition (2) and dispersion (3) layers, the smaller particles are placed on the bodyside of the absorbent articles and the larger particles are located on the opposite side of the absorbent articles.

15 Claims, 11 Drawing Sheets

(51) Int. Cl.

| | | |
|---|---|---|
| *A61F 13/535* | (2006.01) | |
| *B32B 5/02* | (2006.01) | |
| *B32B 5/14* | (2006.01) | |
| *B32B 37/10* | (2006.01) | |
| *B32B 37/12* | (2006.01) | |
| *B32B 37/20* | (2006.01) | |
| *B32B 38/00* | (2006.01) | |
| *B32B 38/08* | (2006.01) | |
| *A61L 15/24* | (2006.01) | |
| *A61L 15/60* | (2006.01) | |
| *C09D 5/44* | (2006.01) | |
| *A61F 13/534* | (2006.01) | |
| *A61F 13/537* | (2006.01) | |
| *A61F 13/53* | (2006.01) | |

(52) U.S. Cl.
CPC .. *A61F 13/15658* (2013.01); *A61F 13/15699* (2013.01); *A61F 13/15723* (2013.01); *A61F 13/534* (2013.01); *A61F 13/5376* (2013.01); *A61F 13/53708* (2013.01); *A61L 15/24* (2013.01); *A61L 15/60* (2013.01); *B32B 5/022* (2013.01); *B32B 5/145* (2013.01); *B32B 37/10* (2013.01); *B32B 37/12* (2013.01); *B32B 37/20* (2013.01); *B32B 38/0004* (2013.01); *B32B 38/08* (2013.01); *C09D 5/4411* (2013.01); *A61F 2013/5307* (2013.01); *A61F 2013/530532* (2013.01); *A61F 2013/530576* (2013.01); *B32B 2260/046* (2013.01); *B32B 2264/0278* (2013.01); *B32B 2307/726* (2013.01); *B32B 2310/021* (2013.01); *B32B 2333/08* (2013.01); *B32B 2555/02* (2013.01)

(58) Field of Classification Search
CPC .......... B32B 2307/726; B32B 2333/08; B32B 2555/02; B32B 5/022; B32B 5/145
See application file for complete search history.

(56) References Cited

U.S. PATENT DOCUMENTS

| | | |
|---|---|---|
| 5,294,478 A | 3/1994 | Wanek et al. |
| 5,422,169 A | 6/1995 | Roe |
| 5,552,012 A | 9/1996 | Morris et al. |
| 5,763,331 A | 6/1998 | Demhartner |
| 6,086,950 A | 7/2000 | Masaki et al. |
| 2002/0090453 A1 | 7/2002 | Muthiah et al. |
| 2003/0018313 A1 | 1/2003 | Tanzer et al. |
| 2003/0129914 A1 | 7/2003 | Ranganathan et al. |
| 2003/0135176 A1 | 7/2003 | Delzer et al. |
| 2003/0135178 A1 | 7/2003 | Hansen |
| 2003/0143324 A1 | 7/2003 | Delzer et al. |
| 2003/0175418 A1 | 9/2003 | Muthiah et al. |
| 2004/0054343 A1* | 3/2004 | Barnett ................. A61F 13/532 604/378 |
| 2005/0003191 A1* | 1/2005 | Ehrnsperger ............ A61L 15/60 428/403 |
| 2005/0027267 A1* | 2/2005 | Van Dyke ......... A61F 13/53713 604/367 |
| 2005/0256758 A1* | 11/2005 | Sierra ..................... A61F 13/53 604/378 |
| 2007/0027436 A1 | 2/2007 | Nakagawa et al. |
| 2008/0312621 A1 | 12/2008 | Hundorf et al. |
| 2008/0312625 A1 | 12/2008 | Hundorf et al. |
| 2008/0312632 A1 | 12/2008 | Fernfors |
| 2009/0087636 A1 | 4/2009 | Yassuda et al. |

FOREIGN PATENT DOCUMENTS

| | | |
|---|---|---|
| WO | WO 1991011163 A1 | 7/1991 |
| WO | WO 1992011831 A3 | 10/1992 |
| WO | WO 2003092757 A1 | 11/2003 |

OTHER PUBLICATIONS

International Search Report within the European Patent Office, completed Jun. 11, 2012 for International Patent Application No. PCT/EP/2012/056859.

"Nonwoven Fabrics: Raw Materials, Manufacture, Applications, Characteristics, Testing Processes," *WILEY-VCH Verlag GmbH & Co. KGaA*, p. 1-12 (2003).

\* cited by examiner

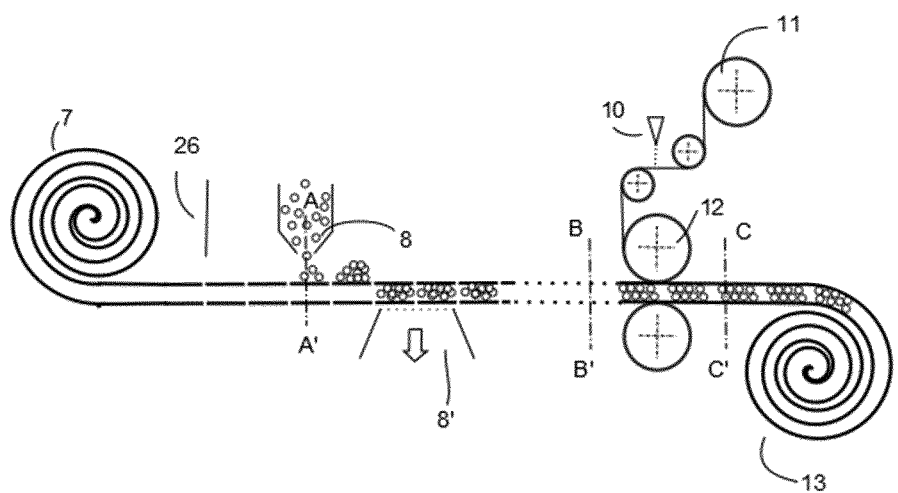
Figure 13
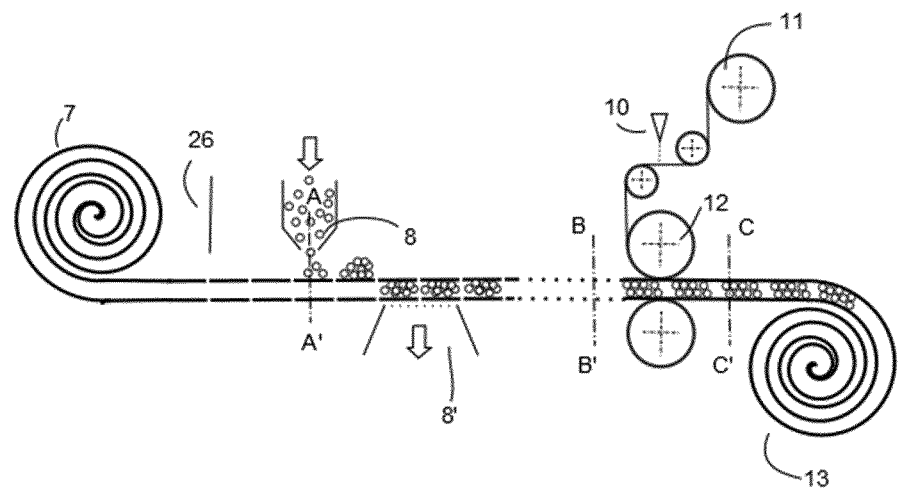
Figure 13 bis

AA'Cut

BB'Cut

CC'Cut

UNITARY ABSORBENT STRUCTURES COMPRISING AN ABSORBENT CORE AND/OR AN ACQUISITION AND DISPERSION LAYER FOR ABSORBENT ARTICLES

FIELD OF THE INVENTION

The present invention relates to absorbent structures comprising a stratum of dispersed super absorbent particles within the absorbent cores and/or acquisition and dispersion systems. The invention also relates to absorbent articles comprising said absorbent structures, the absorbent article is preferably a disposable absorbent article such as sanitary napkins, panty liners, baby diapers, incontinence pads, training pants, sweat pads, medical wound bandage and the like.

BACKGROUND OF THE INVENTION

Conventional absorbent articles are manufactured by combining a liquid permeable or pervious, hydrophilic or semi hydrophilic topsheet (1), a fibrous material, an absorbent core (5) and a liquid impermeable or impervious material backsheet (6). Topsheet (1) and backsheet (6) referring to the relative position of said sheets with respect to the absorbent core (5). Absorbent cores are generally composed of fluff and super absorbent polymer (SAP) particles (21).

Multi-layered absorbent articles may comprise an additional acquisition (2) and dispersion layers (3, 4) (ADL), or conventional ADL (19), having at least 3 functions. The top layer is an acquisition layer (2), which is suitable to rapidly acquire the liquid and transmit it to the distribution layers (3, 4) placed underneath the acquisition layer (2). Said distribution layers allow the liquid to migrate away from the user. A third function is to prevent rewetting by the liquid.

A multilayered ADL is disclosed in Belgian patent BE 1 018 052 which relates to an improved multilayered ADL system comprising a 3 layers acquisition (2) and distribution layers (3, 4) improving the distribution of the liquid (FIG. 2).

Acquisition layers (2) are generally composed of coarse hydrophilic or hydrophobic fibers that quickly transmit the liquid by capillarity to the dispersion layers. Said dispersion layers generally comprise hydrophilic material and fibers suitable in hygiene articles such as profiled or shaped multilobal fibers ranging from 0.7 to 30 dtex and preferably from 1.5 to 7 dtex wherein 1 dtex represents 1 gram per 10000 meters of fiber.

SAP Particles

Typical SAP particles (21) are composed of crosslinked hydrophilic polymers chains capable of absorbing about a 10 time water uptake based on the weight of the dried particles. Hydrophilic polymers are either natural or synthetic polymers or a mixture of both types. Common natural polymers include cellulose-based polymer such as cellulose or starch eventually modified by additional hydrophilic functions for example carboxylates, phosphonate or sulfoxylate. Synthetic hydrophilic polymers are generally a polyether or a polyacrylate based polymer.

SAP particles (21) can advantageously be coated or partially coated. The additional coating improves or provides additional properties to the SAP particles (21) such as a better body fluid absorbing capacity, a better adhesion of the particles to the surrounding, an improved capacity for transportation of liquids or better mechanical properties.

Absorbent Cores

Absorbent cores generally comprise a mixture of SAP particles (21) and a substrate (23) such as fibers, layers, fluff or any combination thereof.

When the absorbent core is wetted, the SAP particles (21) are able to absorb a large amount of liquid; however wet SAP particles (21) are subject to swelling thus forming a gel with the adjacent swollen SAP particles (21). Said gel formation can block the liquid transmission into the interior of the absorbent core.

As consequence, gel blocking leads to potential leakage and/or rewettability issues. To prevent gel blocking and to improve the fluid absorbent capacity of the absorbent core, individual SAP particle (21) have to be sufficiently distant from one another. This is generally obtained by mixing the SAP particles (21) with cellulose-based fluff.

Thinner absorbent core can also be obtained by reducing the amount of fluff used in the composition of the absorbent core. For examples, U.S. Pat. No. 5,763,331 discloses a fluffless absorbent core comprising SAP granular material such as acrylate or a biodegradable material firmly bonded to a support layer such as paper or non-woven fabric. The adhesive used to glue the superabsorbent granular component to the main support layer is applied by spraying.

It is known from US 2009/0087636 an absorbent structure comprising a fibrous substrate and a dispersion of SAP particles however the SAP particles are simply held within the substrate structure and the distribution of the particles is not consistent especially for smaller particles which may move from there location. U.S. Pat. No. 5,294,478 discloses an absorbent structure comprising a fibrous substrate and a gradient dispersion of SAP, however the larger particles are placed on the bodyside and the smaller particles are placed on the opposite side. None of these documents discloses a gradient in which the smaller particles are on the bodyside and the larger particles are on the opposite side.

It is known from US 2003/175418 and US 2002/0090453 a method to prevent particle loss and agglomeration. These patents disclose a process for stably affixing SAP powder onto substrates such as a sheet, film, foam or fiber treated with a curable liquid resin or solution of curable resin such as a thermoplastic resinous powder. SAP powder is applied to the surface of a polymeric material and coated with a curable liquid resin and then cured, by heating. The absorbent film obtained has reduced particle agglomeration and particle loss. Alternatively, the SAP powder is coated with a resinous material and applied to the surface of a polymeric material and cured. Absorbent film obtained accordingly can be interposed between sheets to form an absorbent core.

WO 03/092757 also discloses a method to prepare a fluffless absorbent core composed of sheets of SAP particles and plasticizer. The plasticizer is sprayed onto the SAP particles followed by a thermal pressing. The plasticizer improving the flexibility and structural integrity to the sheet without imparting the rewettability and the acquisition rates of the absorbent core. The method disclosed also facilitates the manufacturing of absorbent articles.

It is also known from U.S. Pat. No. 4,232,674 a liquid absorbent device wherein superabsorbent polymer particles are deposit in predetermined patterns, such as parallel stripes to leave uncovered areas for capillary flow of liquid from saturated to unsaturated areas of the layer.

To improve the liquid retention of absorbent articles, it is also known to prepare a multilayered absorbent core. For example, US 2003/135178 discloses an absorbent laminate core comprising an upper and a lower layer and inner layers wherein one of the inner layers is a central fibrous layer such as tow fibers containing SAP. The other inner layer is a layer selected from an acquisition layer, a distribution layer, an additional fibrous layer optionally containing SAP, a wicking layer, a storage layer, or combinations and fragments thereof.

Multilayered absorbent core may also be obtained from the combination of an absorbent layer or storage layer with a conventional ADL (19) in a unitary structure to form an absorbent core. Unitary absorbent core also generally have a reduced thickness and facilitate the processing of absorbent articles.

Some examples of unitary absorbent cores are disclosed in WO 92/11831. It is known from this document an absorbent article comprising a liquid pervious topsheet, a liquid impervious backsheet and a multi-layered absorbent core positioned between the topsheet and the backsheet. Said absorbent core comprising a multi-layered absorbent body comprising acquisition/distribution layers and a storage layers positioned subjacent each acquisition layer and comprising an absorbent gelling material. A wrapped multi-layered absorbent body is obtained by wrapping the multi-layered absorbent with fluid transporting wrapping.

WO 91/11163 discloses an absorbent structure having an ADL comprising binding means and chemically stiffened cellulosic fibers, preferably curled and a fluid storage layer positioned beneath each ADL comprising SAP particles with an average diameter of 400 to 700 microns and carrier means for the SAP particles.

WO 00/41882 discloses a 2 plies absorbent structure, each ply comprises SAP particles in different concentration and dispersed either homogeneously within a matrix of fibers and binder or placed in discrete locations or zones such as lanes within the structure.

Each ply is composed of several stratums in liquid communication. The different density of the 2 plies creating a capillary tension gradient between the plies.

US 2008/312625, US 2008/312632 and US 2008/3126621 disclose a substantially cellulose free absorbent core comprising 2 absorbent layers each having a substrate comprising SAP particles and thermoplastic adhesive covering the SAP particles. The 2 absorbent layers are jointed together such that a portion of the thermoplastic adhesive of the 2 absorbent layers is in contact. The 2 absorbent layers being combined together such as the respective patterns of absorbent particulate polymer material are offset from one another.

It is known from US 2007/027436 a thin, conformable and flexible absorbent article comprising a fluid permeable topsheet, a backsheet joined to said topsheet about a periphery of said absorbent article and a core disposed between said topsheet and said backsheet, said core comprising a storage layer containing superabsorbent material and an acquisition/storage layer containing superabsorbent material.

With regard to the cited prior art there is a need to improve unitary absorbent structures which provide comfort to the users, a higher absorption ability, mechanical stability, thinness, low rewettability and which are easy to process in an absorbent article.

SUMMARY OF THE INVENTION

The present invention is related to an improved unitary absorbent structure comprising at least one non-woven material such as a fibrous substrate (23) layer having a void volume suitable to be penetrated with super absorbent particles (SAP particles) (21), and adhesives, and said super absorbent particles are dispersed in the substrate layer (23) according to a size distribution gradient along the depth direction or z-direction of said absorbent core (5) and/or acquisition (14) and dispersion (16) unitary layer. Such as the smaller particles are located on the bodyside of the absorbent articles and the larger particles are located on the opposite side of the absorbent articles. The substrate layer comprising the dispersion of SAP particles is used within an absorbent core (5) having a permanent liquid holding capacity and/or an acquisition and dispersion layer (14, 16) having a temporary holding liquid capacity. FIGS. 9, 10, 11, 21, 22 and 23 illustrate different embodiments comprising a distribution of SAP particles (21) in a substrate (23). In a second aspect, the invention relates to a method for producing said absorbent core and/or ADL.

It is an object of the invention to reduce the thickness of absorbent articles by reducing the amount of fluff generally used in absorbent core, generally comprised in the range of 40 to 60 wt. %, without imparting the body fluid absorbing capacity, uptake speed and rewettability of the absorbent core. Further, the absorbent structures according to the invention is fluffless; wherein by fluffless it should be understood that the layer comprises less than 4 wt. % fluff, advantageously the absorbent structures does not comprise any fluff at all and wherein fluff refers to a cellulose fluff.

In a further aspect, the invention relates to an absorbent structure having a high body fluid absorbent capacity without being subject to gel blocking issue.

In a further aspect, the invention relates to an absorbent structure that includes an ADL to form an improved multi-layered absorbent core wherein the ADL and the absorbent layer are unitary and integrated.

In a further aspect the invention relates to absorbent structures or multilayered absorbent structures combined with an additional conventional ADL (19) with or without a fluid holding capacity.

It is a further object of the invention to provide an integrated ready to use absorbent structure able to be directly incorporated in absorbent articles.

DESCRIPTION OF THE DRAWINGS

FIGS. 13 and 13bis: are schemes of a method of a structure production according to the invention.

DETAILED DESCRIPTION OF THE INVENTION

Figure 1:
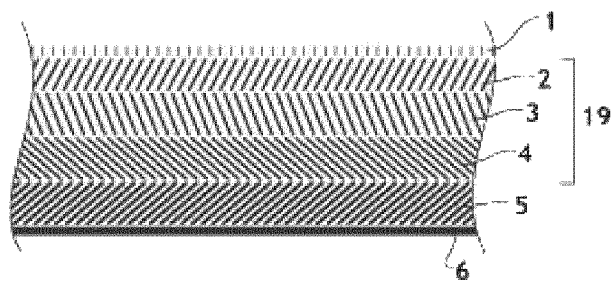
FIG. 1: is a cross-sectional view of a typical absorbent article comprising from top to bottom a liquid pervious topsheet (1) and a liquid impervious backsheet (6), an acquisition and distribution system (2, 3 and 4), an absorbent core (5) generally composed of a mix of fluff and SAP; typically, the amount of SAP range from between 0 to 60 wt. %.
Figure 2:
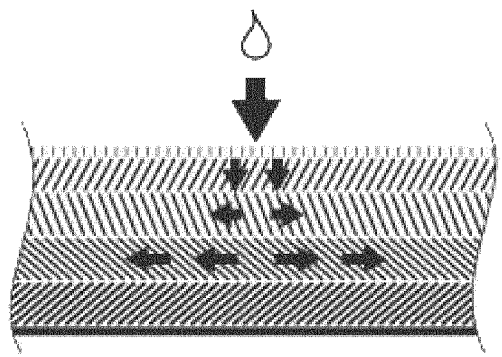
FIG. 2: is a cross-sectional view of a 3 layered conventional ADL (19) comprising from top to bottom an acquisition layer (2) and 2 distribution layers (3) and (4).

A liquid according to the invention comprises, but not limited to, any body fluid such as urine or blood.

The inventors have developed a fluffless absorbent structure comprising a unitary absorbent structure comprising an absorbent core (5) and/or an acquisition and dispersion layers (2, 3), comprising at least one non-woven fibrous substrate (23) layer having a void volume suitable to be penetrated by super absorbent particles, the non-woven fibrous substrate may either be hydrophilic or hydrophobic and said super absorbent particles (21), having a size distribution, are dispersed within the substrate layer (23), according to their particle size distribution gradient along the depth direction or z-direction. The smaller particles are located on the bodyside and the larger particles are located on the opposite side of the absorbent articles. Said fibrous substrate comprising the SAP particles can be integrated in an absorbent core and/or an ADL structure.

The absorbent structure obtained is further coated by a covering layer (22) such as a spunbond, PE film, PET film, polyolefin, multilayer films, coextruded films, carded non-woven or any suitable material and maintained to the core with adhesive.

In addition to the high body fluid holding capacity and the slimness of the absorbent article, there are some other advantages to use the absorbent structure of the invention such as a better conversion, improve performance and reliability due to the dispersion of SAP particles (21) on specific part of the absorbent structure and the absence of fluff. It is also economical advantageous to use such core and/or ADL as fluff is no longer required and extra method steps such as hammer milling to prepare the fluff is unnecessary, additionally, warehousing and packaging cost is reduced as well as the transport cost.

Figure 26:
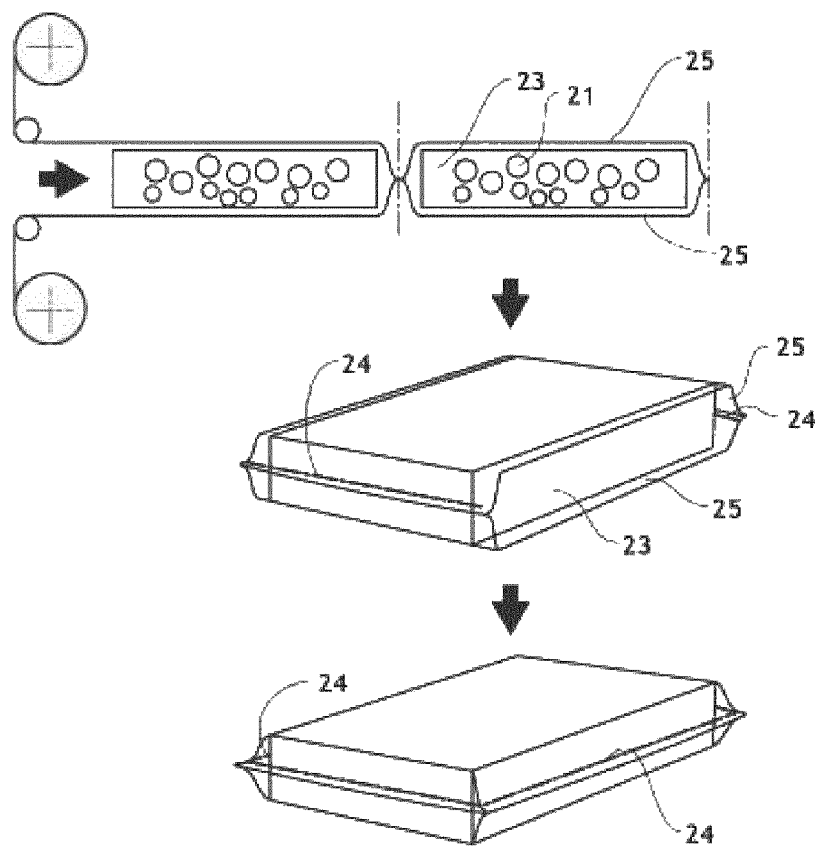
FIG. 26: illustrates the sealing (24) process of individual core by a core wrap material (25).

Advantageously, an absorbent structure according to the invention is a multilayers structure comprising a top layer ensuring a good acquisition and distribution of the liquid; an intermediate layer suitable to prevent the liquid to return to the surface, said intermediate layer is non-porous, wherein non-porous is defined by a void volume value ranging from about 10 to about 600 $cm^3$ of void volume per $m^2$ of substrate (23). The absorbent structure also comprises a porous fibrous bottom layer, wherein porous according to the invention is defined by a void volume ranging from about 0.1 to 20000 $cm^3$ of void space/$m^2$ of substrate (23), preferably from about 600 to about 6000 $cm^3$ of void space/$m^2$ of substrate (23). Said fibrous bottom layer comprising coated or uncoated SAP particles (21) thus forming a SAP stratum beneath the intermediate layer. SAP particles (21) composing the SAP stratum are dispersed within the bottom layer, based on the SAP particle (21) size distribution gradient, wherein the smaller SAP particles (21) are located deeper into the bottom layer and the larger particles remain on the external part of the bottom layer such as the smaller SAP particles are placed on the bodyside of the absorbent articles and the larger particles are located on the opposite side of the absorbent articles. A suitable non-porous core covering layer (22) having a void volume value ranging from about 10 to about 600 $cm^3$ of void volume per $m^2$ of substrate (23) is used to prevent the release of the SAP particles (21), said core covering layer material (22) is maintained to the absorbent structure by adhesive means, ultrasonic welding and/or any suitable method (FIG. 26).

Absorbent structures of the invention comprise SAP particles (21) wherein at least 90%, preferably 95%, and more preferably 98% of the SAP particles (21) have a particle size diameter ranging from about 45 to about 850 μm, preferably from about 100 to about 800 μm and more preferably from about 200 to about 500 μm. Smaller size SAP particles (21) are able to penetrate deeply, i.e. along the z direction, into the inner part of the substrate (23) while the larger size SAP particles (21) remain on the outer part of the substrate (23) or remain on the surface of said substrate (23), thus forming an absorbent stratum based on the SAP particle (21) size gradient. The substrate is reversed such as the smaller particles are located on the bodyside of the absorbent articles and the larger particles are located on the opposite side of the absorbent articles.

Absorbent structure of the invention comprising a SAP particles (21) stratum fully integrated within the absorbent core and/or ADL, allows the preparation of thinner absorbent articles than conventional absorbent cores known by the inventors as said cores generally require a fluff absorption distribution layer or other cellulose based fiber system, for instance curly fibers or a standard ADL system (19) in combination with a fluff holding core.

It has been found that absorbent cores according to the invention have an excellent liquid acquisition property and low rewettability. It is supposed that the SAP particles (21) dispersed in the substrate (23) with a size distribution gradient, wherein the smaller particles are located on the bodyside of the absorbent articles and the larger particles are located on the opposite side of the absorbent articles, are able to prevent the gel formation when the SAP particles (21) are in a swollen state.

Super Absorbent Particles

According to the invention, SAP particles (21) are either uncoated, partially or totally coated.

Commercial available uncoated SAP particles (21) suitable for the invention are Ecotec EK-X EN 67 polymer grade, which is generally used in absorbent cores comprising SAP and fluff in a ratio up to 80 wt. % SAP loadings; Evonik: Favor SXM 10000, Favor 9155.

Advantageously, the SAP particles have a spherical shape such as Aquakeep SA55SX or Sumitomo SA60F from Arkema.

SAP particles (21) can either be incorporated in the absorbent layer or in the ADL or in both the absorbent layers and the ADL.

Absorbent Core

Figure 23:
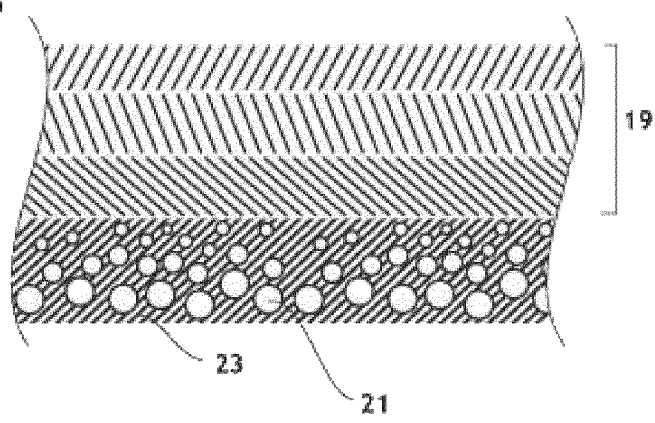
FIG. 23 illustrates an absorbent core comprising a dispersion of SAP within a nonwoven substrate, combined with an ADL.

An absorbent core according to the invention can be obtained by fully penetrating a non-woven substrate (23) with SAP particles (21), thus an additional conventional ADL (19) should be used, as illustrated in FIG. 23.

A substrate (23) fully penetrated with SAP particles (21) according to the invention comprises up to 1000 g/m² of SAP, preferably about 300 to about 500 g/m² of SAP particles (21) depending on the body fluid holding capacity.

To avoid gel blocking, the swollen SAP particles (21) have to be sufficiently distant to be permeable enough to allow liquids, such as body fluids, to go through the absorbent layer. This was obtained by the inventors by distributing the SAP particles (21) within the substrate (23) based on the SAP particles size gradient. Without being bond to any theory, it is believed that only smaller SAP particles (21) penetrate deeply into the substrate (23), along the z-direction, while larger SAP particles (21) remain on the outer part of the substrate (23). Reversing the structure, the smaller particles are on the bodyside of the absorbent articles and the larger particles are located on the opposite side of the absorbent articles. As smaller SAP particles (21) are sufficiently distant from one another, it does prevent gel blocking issue, while larger SAP particles (21) are able to progressively absorb the excess of body fluids.

Preferably, the absorbent structure of the invention can be combined with a conventional ADL (19).

FIG. 23 illustrates an absorbent core according to the invention comprising a non-woven substrate (23) and a dispersion of SAP particles (21) within the substrate (23), depending on the SAP particles (21) size gradient. The absorbent core is further combined with a conventional ADL (19) on top of the absorbent core.

Figure 12:
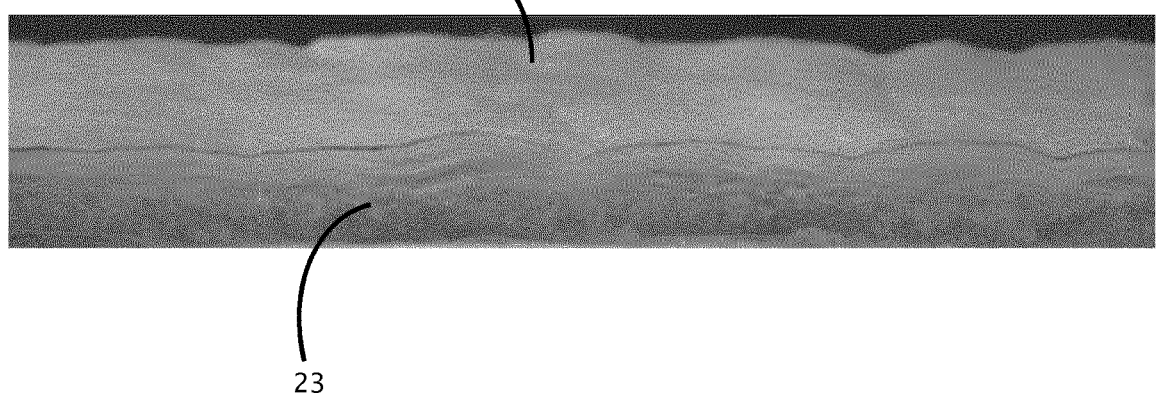
FIG. 12: is a cross sectional image of SAP particles (21) partially penetrated in a substrate having a void volume distribution gradient (18a, 18b, 18c).

FIG. 12 also illustrates an absorbent article according to the invention using a 3 layers ADL structure with SAP particles (21) in a swollen state after liquid uptake.

Acquisition, Dispersion, Layers (ADL)

Figure 9:
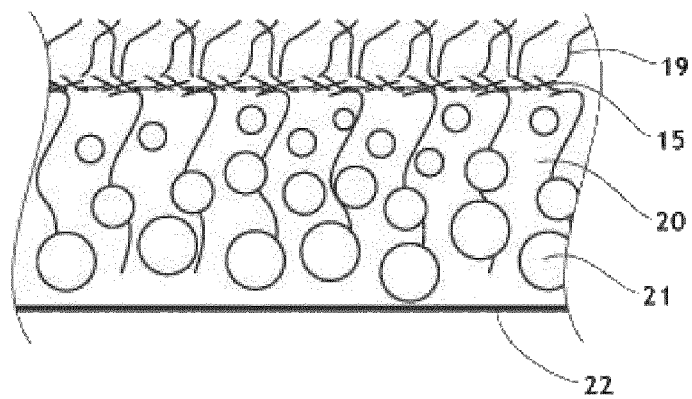
FIG. 9: is a cross-sectional view of a substrate comprising from top to bottom an acquisition and dispersion top layer (19), an rewet layer of smaller void volume space structure preventing the loss of SAP particles (21) and a bottom layer having very large void volume space comprising SAP particles (21) and a covering layer coating the bottom section of the absorbent core.
Figure 10:
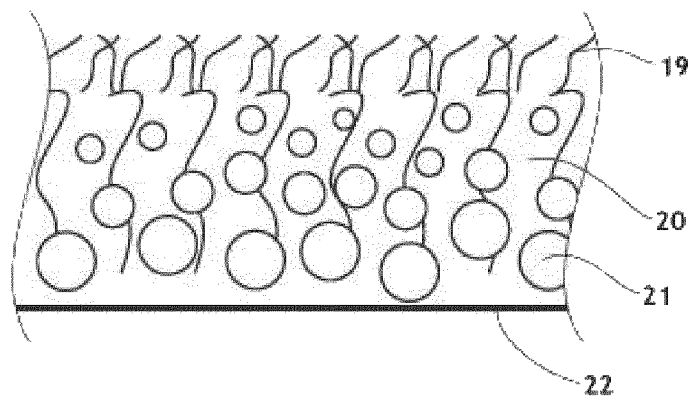
FIG. 10: is a cross-sectional view of a triple layer substrate wherein the fibers defining a void volume distribution gradient (18a, 18b, 18c) partly filled with SAP particles (21), and the bottom of the structure is covered by an additional layer.
Figure 11:
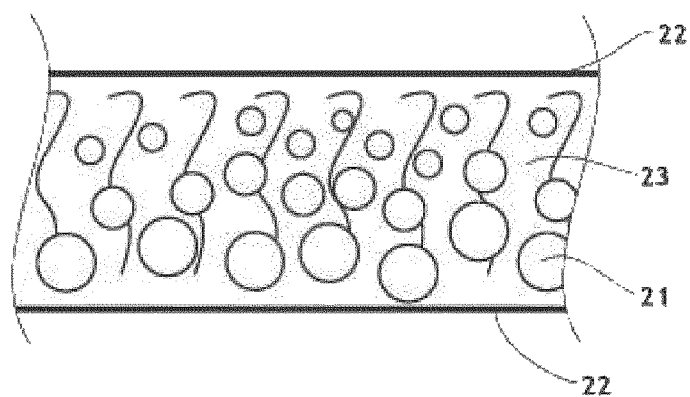
FIG. 11: is a cross-sectional view of SAP particles (21) fully penetrated in a substrate having a void volume distribution gradient (18a, 18b, 18c). The core is covered by non-woven layers on top and bottom part (22).
Figure 22:
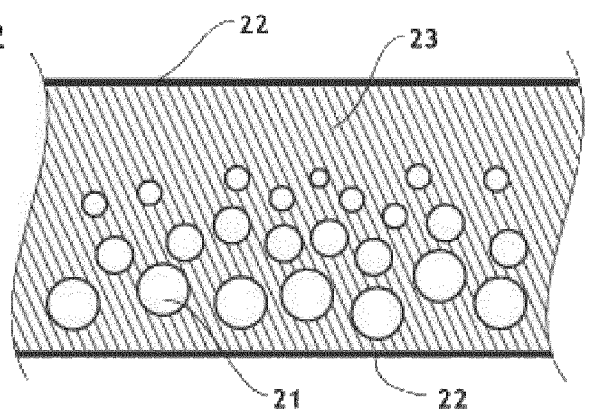
FIG. 22: illustrates an absorbent structure according to the invention coated by a covering layers (22).

In a second embodiment a specific amount and size of SAP particles (21) is dispersed, based on their size dispersion gradient, in a substrate (23) comprising an ADL structure, such as the substrate (23) is partly penetrated with the SAP particles (21). The substrate is used such as the smaller particles are located on the bodyside of the absorbent articles and the larger particles are located on the opposite side of the absorbent articles. FIGS. 9 and 10 illustrate this second embodiment. According to the invention, an ADL comprising a sufficient amount of SAP particles (21) to absorb liquids or body fluids can be directly used as a unitary absorbent structure (FIGS. 9 and 22), said structure comprising an ADL section and an absorbent section comprising the dispersed SAP particles (21). Generally up to 1000 g/m², preferably from about 300 to about 500 g/m² of SAP particles (21) is sufficient to combine in one element an ADL and an absorbent core.

Figure 21:
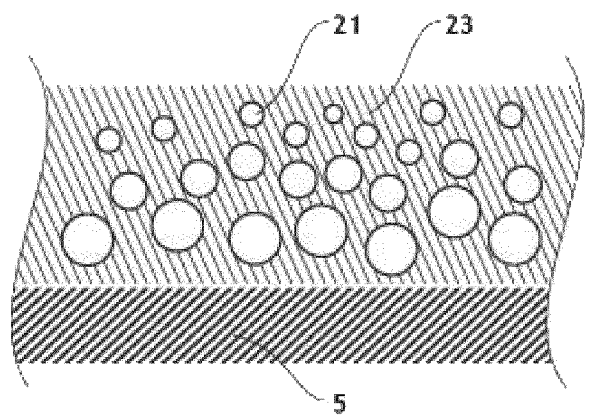
FIG. 21: illustrates an ADL comprising SAP particles (21) dispersed according to the invention, said ADL is positioned on top of a conventional absorbent core.

The ADL can also comprise low amount of SAP particles (21) which serve as a temporary storage or surge layer (20) (FIG. 21). Generally between 0.1 to 300 g/m², preferably from about 100 to about 200 g/m² is considered as a low amount of SAP particles (21). In the latter case, an additional absorbent core has to be combined with an ADL. Suitable ADL should absorb water or liquids and slowly releasing it to the absorbent core.

Typically, ADL are multi-layer structures comprising an acquisition layer (2) and dispersion layers (3, 4). In a preferred mode, the ADL comprising a dispersion of SAP particles (21) is a 3 layers structure composed of one acquisition layer (2) and 2 diffusion (3) layers.

Figure 3:
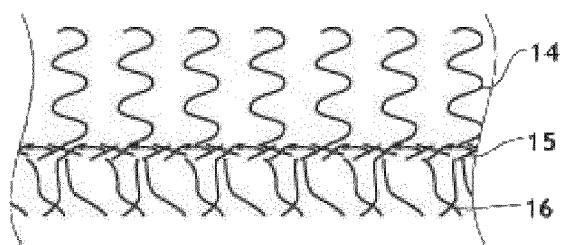
FIG. 3: is a cross-sectional view of a substrate comprising from top to bottom a triple layer acquisition (14), rewet (15) and distribution (16) layers.

In a particular embodiment, a triple layers ADL according to the invention can comprise an acquisition layer (14), a rewet layer (15) and a distribution layer (16) are illustrated in FIG. 3.

The top layer is a very porous acquisition layer (14) allowing fluids to easily penetrate the structure.

The intermediate layer is a non-porous diffusion layer preventing the fluid from going back to the top surface. By non-porous according to the invention is defined by a void volume ranging from about 10-600 cm³ of void space/m² of substrate (23). The diffusion layer is also very hydrophilic, so that the liquid is spread over the core.

The bottom layer comprises profiled, or multilobal, fibers to improve the liquid distribution over the absorbent core. Non limiting examples of commercially available multilobal fibers are 4DG 6 dn, 4T 3 dn, trilobal 6 dn, pentalobal 6 dn, quadfill 7 dt, preferably, the fiber is a trilobal 6 dn or pentalobal 6 dn fiber and other shapes.

Figure 4:
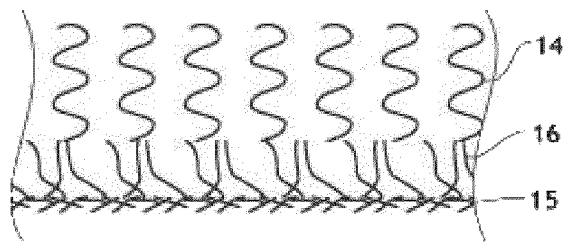
FIG. 4: is a cross-sectional view of a substrate comprising triple layer acquisition (14), distribution (16), rewet (15) layers.

In another embodiment according to the invention, a triple layers ADL comprising an acquisition (14), distribution (16) and rewet (15) layers, as illustrated in FIG. 4.

The top layer is a very porous acquisition layer (14) thus allowing fluid to penetrate into the absorbent core.

The intermediate layer is a dispersion layer comprising profiled fibers, thus improving the distribution of the liquid to the bottom layer.

The bottom layer is a non-porous layer comprising very fine fibers, preventing liquid from going back to the surface. It is also very hydrophilic, so that the liquid is spread over the core.

Figure 5:
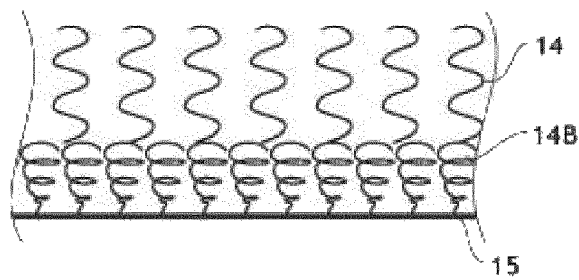
FIG. 5: is a cross-sectional view of a substrate comprising from top to bottom a triple layer acquisition (14) and rewet (15) layers.

In another embodiment according to the invention, a triple layers ADL comprising 2 acquisitions layers (14) and a rewet layer (15) is illustrated in FIG. 5.

The top layer is a very porous acquisition layer (14) allowing fluid to penetrate into the absorbent structure.

The intermediate layer is also an acquisition layer (14) that is semi porous, wherein semi porous according to the invention is defined by a void volume ranging from about 300 to about 500 cm$^3$ of void volume/m$^2$ of substrate (23), however said intermediate layer is characterized by a void volume distribution gradient (18a, 18b, 18c) thus creating a funnel for the liquid transport towards the core.

The bottom layer is non-porous, and composed of very fine fibers preventing liquid from going back to the surface. Preferably, the bottom layer is calendered, to even more reduce the void volume on the surface, preventing the liquid of the core returning to the surface. Said bottom layer is preferably hydrophilic, allowing the liquid to spread over the core.

Figure 6:
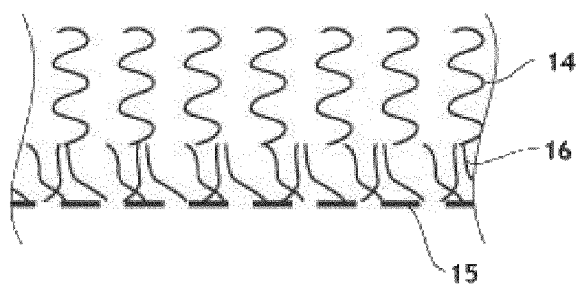
FIG. 6: is a cross-sectional view of a substrate comprising from top to bottom a triple layer acquisition (14), distribution (16) and rewet (15) layers with the third layer partly hydrophobic.

In another embodiment according to the invention, the absorbent structure comprises a triple layers ADL also comprising an acquisition (14), distribution (16) and rewet (15) layers, as illustrated in FIG. 6.

The top layer is a very porous acquisition layer (14) suitable to allow body fluids to penetrate into the absorbent structure.

The intermediate layer is a layer suitable for the distribution and spreading of the liquid to the bottom layer and to the core. The bottom layer is a non-porous layer composed of a blend of fine hydrophilic and hydrophobic fibers, blocking the liquid from going back to the surface.

Figure 7:
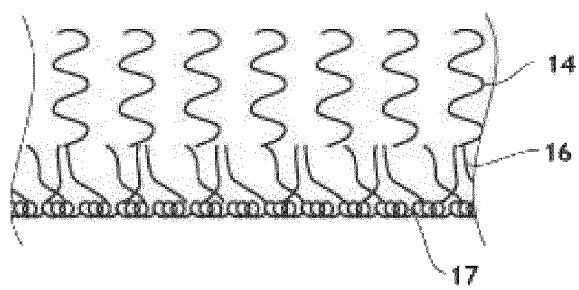
FIG. 7: is a cross-sectional view of a substrate comprising from top to bottom a triple layer acquisition (14), distribution (16) and absorption (17) layers.

In another embodiment according to the invention, the absorbent structure comprises a triple layer, acquisition (14), distribution (16) and absorption (17) layers as illustrated in FIG. 7.

The top layer is a very porous acquisition layer (14) allowing body fluids to penetrate into the absorbent core.

The intermediate layer is a distribution layer (16) comprising fibers to ensure the whole surface of the distribution layer (16) is used.

The bottom layer comprises a blend of fibers including viscose absorbing fibers, to temporarily store the liquid in said bottom layer, thus creating a buffer before the liquid is transferred to the absorbent core.

Figure 8:
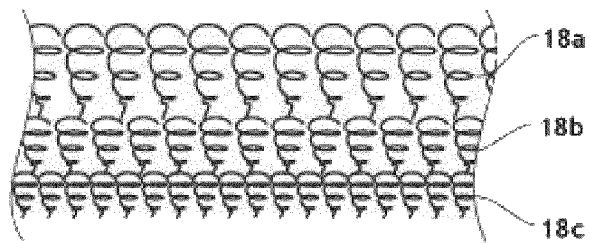
FIG. 8: is a cross-sectional view of a substrate comprising from top to bottom a triple layer blend of polyester and polyolefin defining a void volume gradient (18a, 18b, 18c).

In another embodiment illustrated in FIG. 8 the triple layer ADL comprises a blend of polyester and polyolefins fibres defining a triple layer system defining a void volume gradient (18a, 18b, 18c) of 3000, 1000 and 300 cm$^3$ of void volume/m$^2$ of substrate surface (23), said void volume gradient (18a, 18b, 18c), creating a funnel for the liquid. This results in a higher liquid uptake speed.

The fibers used give a good resiliency and resistancy to pressure, creating a distance between core and top of the diaper, resulting in a dry surface.

ADL suitable for the invention are fluffless and ensure a fast liquid uptake, and good rewet properties, so that liquid is prevented from going back to the surface and maintain the top surface dry. It also makes sure the liquid is well spread and distributed, so that the total core is used to its maximum.

Absorbent Structures

An absorbent structure according to the invention can combine an absorbent section and an acquisition (14) and dispersion (16) section. In these specific embodiments, illustrated in FIG. 22, the absorbent structure is composed of a mono or multi layered non-woven fibrous substrate (23) such as polyester or poly polyethylene terephthalate (PET), polyethylene (PE), polypropylene (PP), coPP, PET/PE, PET/PP, PET/cop, PP/PE, PLA, PLA/PP, PVA, viscose, cotton, wool, PET/coPET, acetate, PTE, PVC, Bamboo, PBT, PA, Acryl, Modacryl, and/or regenerated fibers forming an interpenetrating network and SAP particles (21) and from about 0.1 to 50 g/m$^2$, preferably from 0.7 to 25 g/m$^2$ and more preferably from about 2 to 7 g/m$^2$ of adhesive. Preferably the absorbent structure does not comprise fluff at all. It is possible to incorporate a high quantity of SAP particles (21) within the absorbent layer because of the fibrous nature which allows the absorption of liquids without being subject to gel blocking due to swelling of the SAP particles (21). In a preferred embodiment of the invention, the absorbent structure comprises from about 25-300 g/m$^2$, but preferably from about 60 to 150 g/m$^2$ of ADL and/or substrate (23); from about 0.1 to 1000 g/m$^2$ of SAP particles (21), a preferred quantity of SAP particles (21) for baby diapers or adults incontinence ranges from 100 to 500 g/m$^2$, from 10 to 200 g/m$^2$ in feminine care products and from about 200-400 g/m$^2$ for wound dressing. Generally, the absorbent structure comprises from about 10 to 60 g/m$^2$ of a core covering layer (22).

Examples of commercially available fibers suitable to make the non-woven substrate (23) are Acryl Amicor 3.0n; Asota L10D; Eastlon SN-3450CMP1 4.0 dn; Fibervisions ES-C Cure 2.2 dt; Fibervisions ES-DELTA REPEAT II 5.7 dt 40 mm; Grisuten 22 3.3 dt 60 mm; Huvis LMF U16 6 dn 51 mm; Huvis LMF V16 4 dn 51 mm; Huvis OEPO1 N215 2.0 dn; Ingeo PLA SLN2660E2 6.0 dn; Invista 295 6.0 dn; Meraklon PP Blend PH/HW 4.4 dt; PES Greenfiber 6.7 dt; Tesil 84M 6.7 dt; Trevira 200 6.0 dt; Viscocel 3.3 dt 40 mm; Wellman H1295 7 dt; Wellman T0745 17 dt 60 mm; Wellman H7112 12 dt; Wellman H8015 7 dt 60 mm.

An absorbent structure according to the invention has a lateral dimension ranging from 0.1 to 800 mm but not limited to these dimensions. Depending on the different application, said absorbent structure typically has a lateral dimension of 50 to 180 mm for baby diaper products; from 30 to 250 mm for adult incontinence products; from 30 to 90 mm for feminine care products and from 100 by 100 mm$^2$ or 200 by 300 mm$^2$ for wound dressing.

Preferably, the non-woven fibrous substrate (23) is a triple layer substrate (23) comprising a top layer, which has an acquisition (14) and dispersion (16) functions for a fast liquid acquisition and a good distribution of the liquid over the total surface of the intermediate layer.

The intermediate layer is preferably very hydrophilic so that the liquid is able to spread over the core. Said intermediate layer is also non-porous, to prevent the fluid to return to the top surface and to maintain the SAP particles (21) within the bottom layer during application, but also during the use of the absorbent article, once the SAP particles (21) are swollen by liquid.

The bottom layer is a very porous structure suitable for being penetrated with SAP particles (21), said bottom layer serves as a storage layer (20) (FIG. 9).

In another embodiment, SAP particles (21) penetrate the void volume gradient (18a, 18b, 18c) of fibers network. Smaller particles will penetrate deeper than bigger particles due to the void volume gradient of fibres (18a, 18b, 18c). After flipping the structure, the top side of the fibrous structure will be substantially free of SAP particles (21) and can further serve as acquisition (14), distribution (16) and rewet (15) layer.

In a further embodiment, SAP particles (21) can completely penetrated a monolayer or multilayers, preferably dual or triple layer structure. The top and bottom part of the structure being covered by a covering layer (22) such as a spunbond, non-woven, spunlace or a film of polypropylene, polyethylene or PET, to prevent said SAP particles (21) from transferring to the outside of the absorbent.

In a preferred embodiment, the multilayers substrate (23) has a porous top layer suitable to allow the penetration of the SAP particles (21) within the substrate (23) while the bottom layer, or one of the intermediate layer, is non-porous to prevent the loss of SAP particles (21) by transfer through the substrate (23). Advantageously, at least one additional covering layer (22) is used to prevent any loss of SAP particles (21). In order to have more coverage additional 2 layers can be used. If 2 layers are used, the edges of said covering layers (22) are glued to seal the structure. If one structure covering layer (22) is used, said layer is fold to wrap the structure and the edges are glued to seal the structure. The most ideal is to wrap the structure on a C shape (C-wrap) but not necessary (FIG. 26).

Method to Prepare an Absorbent Structure

A method to prepare an absorbent structure suitable for the invention is illustrated in and comprises the step of:

Unwinding (11) the fibrous substrate (7), and eventually perform a mechanical opening of the substrate which can be applied before or after the deposition of the SAP particles.

Covering the substrate (7) with the SAP particles (21) by powder scattering (8); drum formation, through vacuum technology (8') of a standard diaper line; gravity feed; high pressure spray gun (air pressure cannon). The SAP particles (21) are then dispersed in the substrate (7) by means of vibrations and/or the use of a vacuum table (8'). From 0 bar to 150 bars; preferred below 10 bars The SAP particles (21) are maintained in the fibrous substrate (7) by entrapment or entanglement and/or after an optional binding step wherein the SAP particles (21) are bonded to the non-woven fibres by the addition of glue which can be applied prior or after the deposition of the SAP. Preferably the glue is applied by a spray gun.

Winding the absorbent structure (13).

Optionally, calendering the product to create a channel structure in the longitudinal direction.

Preferably, the coated or uncoated SAP particles (21) are glued to the fibers of the ADL layers. None limitative bonding method include powder coating and thermo bonding, heat treatment, spray coating, powder scattering, reactive glue (activation and curing) or any combination thereof. The SAP dispersion is preferably done by the combination spray gun and vacuum table.

After the step of covering and dispersing SAP particles onto the substrate, the substrate is preferably covered with an additional covering layer by:

Unwinding (11) a core covering layer material (22).

Applying an adhesive (10) on the inner face of the core covering layer (22) and/or the substrate surface (7).

Covering the substrate (7) with said core covering layer material (22).

Ensuring the adhesion by pressure (12).

Suitable device (see FIGS. 13 and 13 bis)

The devices (FIGS. 13 and 13 bis) suitable to prepare the absorbent structure of the invention can be employed either in line or off line of an ADL and/or core production line or of a diaper or feminine care production line.

FIGS. 13 and 13 bis also illustrate an optional precutting step (26) of the substrate indeed the cutting can be performed after the addition of SAP particles.

SAP Particles

SAP particles (21) of diameter ranging from about 45 µm to about 850 µm, preferably from about 100 to about 800 µm and more preferably from about 200 to 500 µm and having an average diameter size of about 300 to 600 µm are preferred as the small particles effectively penetrate the ADL while larger size particles remain on the outer side of the diffusion layer thus forming a storage stratum (20). Advantageously SAP particles (21) of different size specification can be successively dispersed into the substrate. Smaller size specification SAP particles (21) can be dispersed in a $1^{st}$ step and in a $2^{nd}$ step larger size specification SAP particles (21) can be dispersed within the substrate.

Adhesive

Suitable glue according to the invention has to provide a good adhesion, has to be permeable to liquids in order to allow the liquids to reach the absorbent layer and has to have an elongation at break of at least 100%, preferably of 600 to 1800% in order to prevent gel blocking issue when the SAP particles (21) are swollen by body fluids. Preferred glue are water based glue and solid powder glue, which are pulverized to bond the SAP particles (21). Suitable commercially available adhesives are, but not limited to, Bostik H4245; Bostik H20028; Bostik H4322 or Füller Full-Care 8400A or Henkel Euromelt 357.

Method to Produce Multiple Absorbent Cores and/or ADL

A method to produce an absorbent structure comprising an absorbent core and/or an ADL according to the invention is described in FIGS. 13 and 26.

Advantageously, said method can be adapted to produce profiled absorbent core and/or an ADL.

Figure 14:
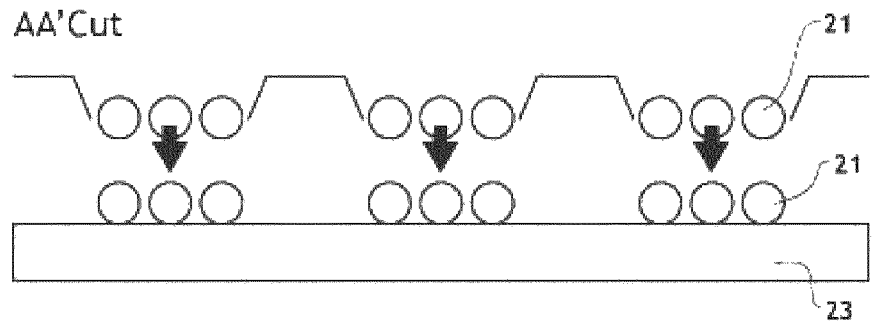
FIG. 14: is a scheme of a dosing system for the SAP particles (21), illustrating the deposit of the SAP particles (21) along the y-direction, or lateral dimension, of the non-woven substrate.

The unwinding substrate layer (7) has to be sufficiently wide to process several absorbent structures in parallel. It is therefore possible to scattering and supply SAP particles (21) in a discontinuous manner over the width or lateral dimension or y direction of the substrate (7), as illustrated in FIG. 14.

The method comprises the step of:

Unwinding the fibrous substrate (7). Depending on the void volume distribution of the substrate (7), the substrate (7) can be maintained upwards during the process in order to prevent the loss of SAP particles (21).

Partially deposit an amount of SAP particles (21) on the substrate (7) over the lateral, or y-direction, of the substrate (7) by powder scattering (8), by a vacuum drum (8'), by gravity feed (8), or by a high pressure system such as spray gun or air pressure cannon (FIG. 13 bis).

Glue can be added to the substrate prior of after the SAP deposition step. Preferably the glue is applied on the substrate by a spray gun.

Applying vibrations and vacuum (8') to the substrate to ensure a distribution of the SAP particles (21) within the substrate (7), said SAP particles (21) are maintained in the fibrous substrate (7) by entrapment or entanglement and/or after an optional binding step wherein the SAP particles (21) are bonded to the non-woven fibres by the addition of glue.

Applying a hotmelt adhesive (10) on the substrate (7) surface and/or on the core covering layer (22).

Unwinding (11) a core covering layer material.

Covering the substrate (7) with said core covering layer (22). Where the SAP particles (21) are present, the hotmelt adhesive will bond the covering layer (22) to the substrate (7), binding the SAP particles in the totality (21). Where the substrate (7) is free of particles the adhesive will bond the core covering layer (22)

material to the substrate layer (7) on part of the substrate (7) essentially free of SAP particles (21) thus sealing the absorbent core. Preferable with sealing; as the sealing prevents SAP particles (21) from falling out when this cutting occurs and prevents the SAP particles (21) from moving to the sides.

Figure 15:
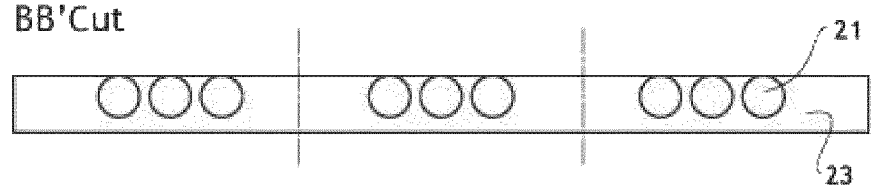
FIG. 15: is a cross sectional view of a discontinuous application of SAP particles (21) on a substrate for the production of multiple absorbent cores. The core is covered by a hot melt adhesive and a core covering layer (11). The cutting line for the formation of individual core is also indicated.
Figure 16:
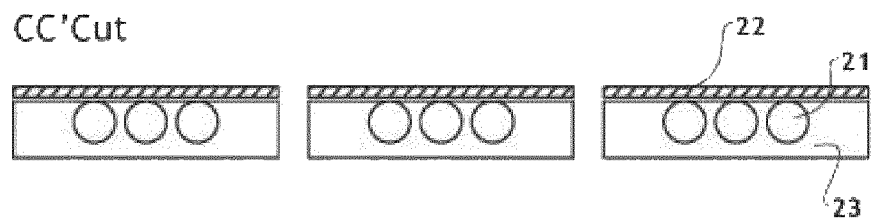
FIG. 16: is a cross sectional image of 3 individual profiled absorbent cores.

Cutting the layer where substrate (7) essentially free of SAP particles (21) to obtain individual cores as illustrated in FIG. 15.

Further, to prevent sideway migration of the SAP particles, it is advantageous to add pressing barriers obtained by heating, pressurizing or ultrasonically.

Figure 17:
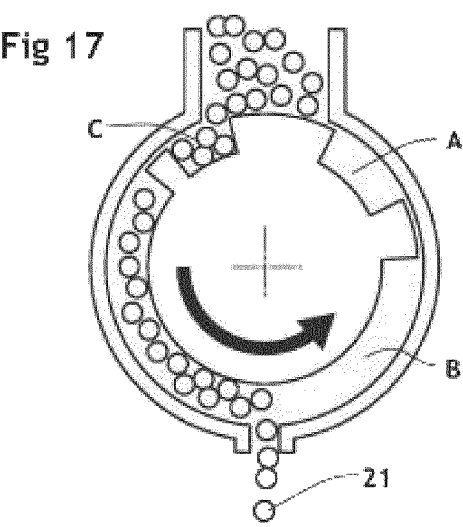
FIG. 17: is a detail view of the supply roll used for the powder scattering of SAP particles (21) to create a profiled core.

Advantageously a SAP particles (21) distribution profile can be obtained along the length or longitudinal dimension or x-direction of the absorbent structure. Said distribution profile is done by creating a profile in the supply roll used to deposit the SAP particles (21) on the substrate (7) by a powder scattering step. FIG. 17 illustrates a supply roll according to the invention wherein the front, middle and back sections of the substrate (7) will receive a specific amount of SAP particles (21).

The transition between the sections of different concentrations will be homogenized upon applying vibrations and vacuum (8') during the dispersion step.

Figure 18:
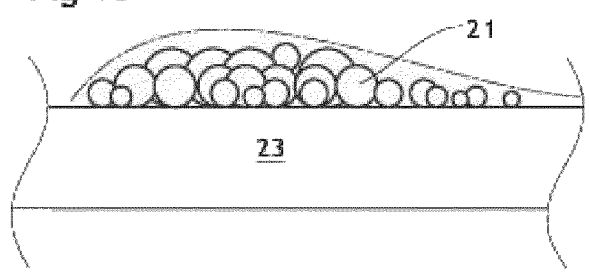
FIG. 18: is a cross sectional image of a profiled absorbent core along the x-direction or longitudinal dimension.

As illustrated in FIG. 18, a profiled absorbent structure along the longitudinal dimension (x-direction) can be obtained, using said supply roll, said structure comprising a higher amount of SAP particles (21) at the front and the middle, and a lower amount of SAP at the back of the diaper.

The profiled absorbent structure obtained accordingly comprises an absorbent part comprising SAP particles (21) partially penetrated in a nonwoven substrate (23) and an upper part serving as an ADL covered with a covering layer (22). The covering layer (22) may be maintained by a hot melt adhesive. Thus the profiled absorbent structure can be directly used in absorbent articles.

Figure 25:
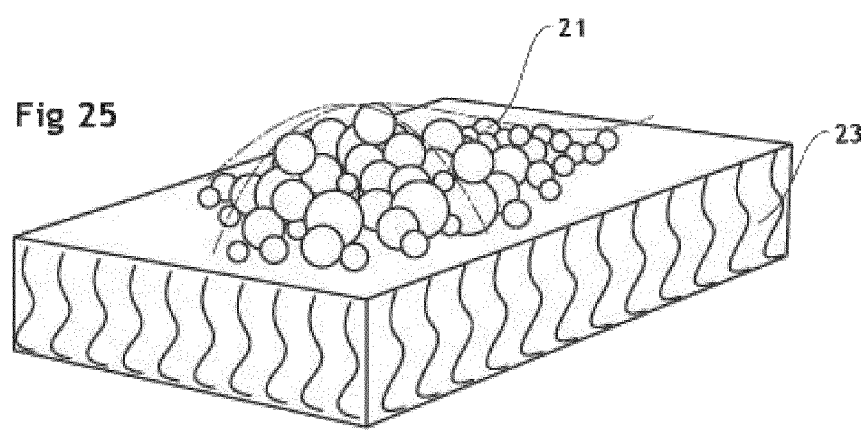
FIG. 25 illustrates SAP particles deposited on a nonwoven substrate.

Preferably, the deposit of SAP particles (21) on the non-woven substrate (23) has a lateral and a longitudinal profile as illustrated in FIG. 25. As after the dispersion of the SAP particles (21) by applying vacuum (8') and/or vibration to the substrate, the absorbent structure obtained will have an optimized absorbing ability due to the amount of SAP particles (21) dispersed within the substrate (23) according to the x, y and z-direction gradient dispersions.

Figure 19:
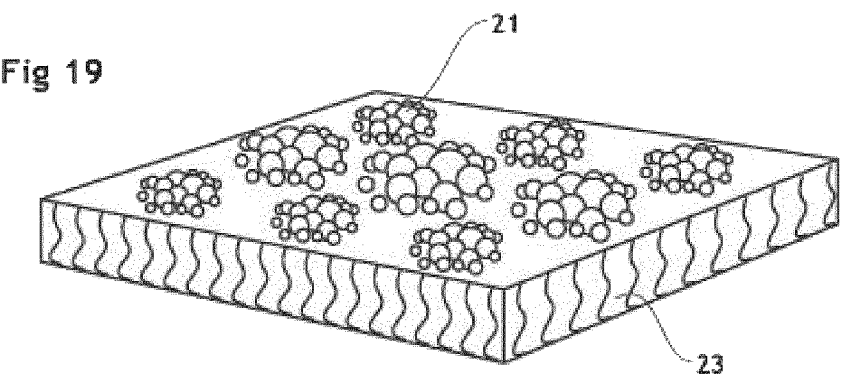
FIG. 19: is a top view of a patterned absorbent core layer in the x-y plan.
Figure 20:
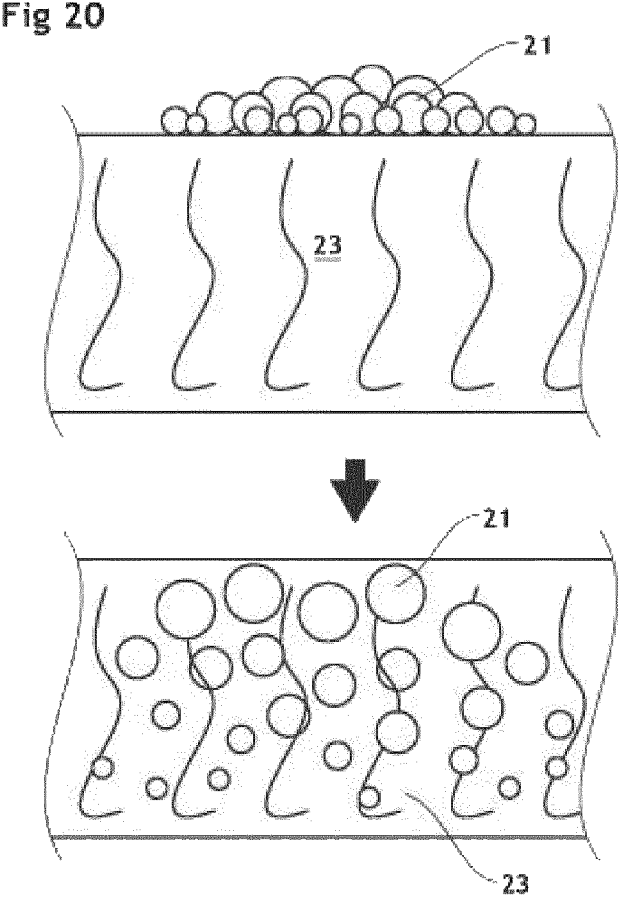
FIG. 20: illustrates the deposit of SAP particles (21) on a non-woven substrate prior to the dispersion step.

In a preferred embodiment, the SAP particles (21) are also dispersed in discrete zones along the x-direction and/or y-direction of the substrate (23), each discrete zone being separated from one another (FIG. 19). Following the dispersion step, the resulting absorbent core and/or ADL comprises, different motifs such as bands, or channels free of SAP particles (21) thereby facilitating the flow and wicking of the fluid (FIGS. 19 and 20).

Figure 24:
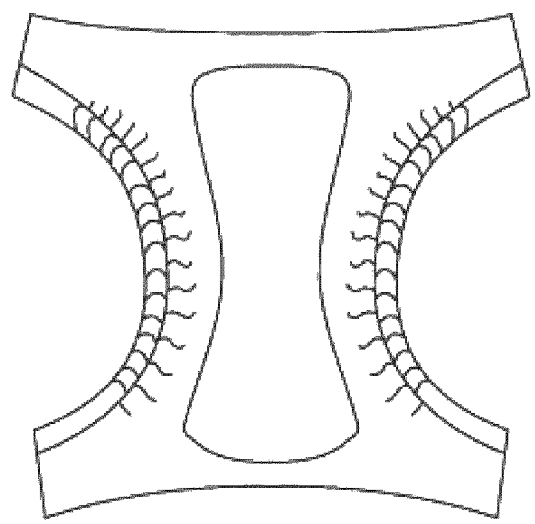
FIG. 24: is a top view of a body shaped absorbent article.

The absorbent structure can be used as a ready to use absorbent structure for absorbent articles (FIG. 26) and can easily fitted in body shaped absorbent articles (FIG. 24).

EXAMPLES

Examples of SAP particles (21) suitable for the invention are FAVOR SXM 10000 and FAVOR SXM 9155 from Evonik.

FAVOR SXM 10000 is a partially neutralized cross-linked sodium polyacrylate polymer having a size dispersion of approximately:

| Particles size (μm) | % |
| --- | --- |
| SAP > 850 μm | <1% |
| 600 μm < SAP < 850 μm | 20-45% |
| 300 μm < SAP < 600 μm | 30-60% |
| 150 μm < SAP < 300 μm | 5-25% |
| 45 μm < SAP < 150 μm | <3% |
| SAP < 45 μm | <1% |

FAVOR SXM 9155 is a cross-linked sodium polyacrylate polymer having a size dispersion of approximately:

| Particles size (μm) | % |
| --- | --- |
| SAP > 850 μm | <1% |
| 600 μm < SAP < 850 μm | ~35% |
| 300 μm < SAP < 600 μm | ~44% |
| 150 μm < SAP < 300 μm | ~16% |
| 45 μm < SAP < 150 μm | ~3% |
| SAP < 45 μm | <1% |

Other examples of SAP particles suitable for the invention are BASF E2535-12

| Particles size (μm) | % |
| --- | --- |
| SAP > 560 μm | ~8% |
| 400 μm < SAP < 560 μm | ~51% |
| 300 μm < SAP < 400 μm | ~23.5% |
| 220 μm < SAP < 300 μm | ~9% |
| SAP < 220 μm | <8.5% |

Arkema Aquakeep SA55SX

| Particles size (μm) | % |
| --- | --- |
| SAP > 560 μm | ~30% |
| 400 μm < SAP < 560 μm | ~41% |
| 300 μm < SAP < 400 μm | ~24% |
| 200 μm < SAP < 300 μm | ~4% |
| 100 μm < SAP < 200 μm | ~0.5% |
| SAP < 100 μm | <0.5% |

Arkema Sumitomo SA60F

| Particles size (μm) | % |
| --- | --- |
| SAP > 560 μm | ~12% |
| 400 μm < SAP < 560 μm | ~30% |
| SAP < 400 μm | ~58% |

The SA55SX is coarser than the SA60F=30%>560 μm for the SA55SX vs 12%>560 μm for the SA60F.

The most adapted particles size for support impregnation should be below 500 μm. In this regard the references Aquakeep SA60F and BASF ones are the most adapted for the impregnation. However Evonik types can be made with the same distribution and when we take a particle size cut in the Gauss distribution curve. We can also impregnate as well all the other SAP types.

ADL Insertion or Substitution

Commercial absorbent articles are compared to a same product wherein the ADL, if any, is substituted by an ADL of the invention. Insertion of a new ADL is performed as follow:

The top sheet of the diaper is cut and carefully opened along the ADL, if any is present in the diaper. To prevent any damage to the absorbent core, the front part of the diaper must remain intact, in order not to affect the leakage.

The ADL is carefully removed and its position is indicated on the topsheet using pins.

A new ADL to be tested is then placed into the diaper.

The diaper is then sealed and glued if necessary.

Spreading and Absorption Capacity Measurements

Spreading represents the distribution in length of liquid in the absorbent device.

Absorption capacity represents the amount of liquid which can be hold by the absorbent device before leakage occurs.

Diapers

Prior to the measurement, the diapers are removed from their packaging for at least 1 hour to fully reloften the diaper.

The thickness of the diaper is measured under a load of 0.5 kPa at 3 different positions: front, center and back area.

Absorption Before Leakage Test (ABL)

The acquisition capacity and spreading measurement method is based on a method developed by Courtray. For each test runs 4 samples are measured.

Spreading value is measured as the total length of the dispersion of the liquid and absorption capacity of diapers were measured on mannequins using an automatic dosage system which determines the doses and times.

When a leakage occurs, the leak is detected by the controlling system and a signal is sent to the monitoring system which records the absorption capacity of the absorbing device. absorption capacity recorded is then compared to the absorption capacity of an original diaper.

The system is calibrated prior to any test, or after every three series of tests.

A saline solution is used as a test fluid. The amount of test fluid used depends on the mannequin sizes and diaper types.

| Type | Weight category (kg) | Mannequin size | Amount per doses of NaCl solution (ml) at 0.9% |
|---|---|---|---|
| Mini | <6 | 1 (5 kg) | 30 |
| Midi | 4-9 | 1 (5 kg) | 45 |
| Maxi | 8-18 | 2 (7 kg) | 60 |
| Maxi plus | 10-20 | 2 (7 kg) | 65 |
| Junior | 12-25 | 3 (9 kg) | 70 |

The diapers are weighted and the thickness is measured at the 3 different zones.

If necessary, the ADL is replaced as previously mentioned.

The diaper is placed and adjusted on the mannequin.

The mannequin is laid on its back or its abdomen depending on the measurement to be performed.

Test fluid is applied to the diaper by at least 3 consecutive doses. The flow of the test fluid for each dosing is of 200 ml/min (+/−5 ml/min) and each dosing is spaced by an interval of 5 min. The first dose is applied to the abdomen, the second dose is applied on the back and the third and other doses are applied to the abdomen.

The method can also be adapted to simulate a boy or a girl. The absorption capacity is calculated as the weight of the wet diaper minus the weight of the dry diaper. The spread is measured as the total length of the dispersion of the liquid.

Acquisition Time and Rewet Measures of Absorbent Devices.

The acquisition time is the time required for the test liquid to penetrate the test sample.

The rewet is the amount of liquid absorbed by filter paper on the surface of the diapers at a certain load.

The apparatus comprises test plates with a tube and weighting 2×4.00 kg; a cushion is used as a support; a 140×190 mm filter plate obtained from S & S under the reference Type 604; Test liquid is obtained from Kanga under the reference LMT-003. The test is performed either on commercial diapers or specific samples.

Hygiene Diapers

Method

The tests are based on the Hy-Tec method.

Five samples are tested in parallel. The diapers are weighted and the thickness of the diaper is measured, under a load of 0.5 kPa, at 3 different zones: the front, the mid and the back of the diaper.

If required, an ADL originally present in the diaper may be substituted by a new ADL of the invention as previously described.

The center point of the diaper is marked and the pee-point is determined as being positioned 2.5 cm forward relative to the center point.

The diaper is laid flat on a cushion using weights and plates. The test plate is positioned parallel to the diaper and leveled, ensuring that the center of the tube is on the pee-point. The leg cuffs are pulled from under the sheet so that it is located next to the plate and any small leaks can absorb. The weights are placed on the plate on both sides of the tube.

The quantity of test liquid is measured with the automatic dispensers and added through the tube within the weight plate, thus simulating a pee point. The amount of liquid dependents on the type and size of the diapers (see Table).

| Type | Weight category (kg) | Load on diaper (kg) | Amount of 0.9% NaCl solution (ml) | Load on the filter papers (kg) |
|---|---|---|---|---|
| Newborn | | 2 × 4 | 30 | 2 × 4 |
| Mini | <6 | 2 × 4 | 40 | 2 × 4 |
| Midi | 4-9 | 2 × 4 | 50 | 2 × 4 |
| Maxi | 8-18 | 2 × 4 | 70 | 2 × 4 |
| Maxi plus | 10-20 | 2 × 4 | 70 | 2 × 4 |
| Junior | 12-25 | 2 × 4 | 70 | 2 × 4 |

The samples are compared to an original diaper which was not manipulated and remained intact and to a reference diaper for which the ADL has been removed and reinserted as previously described.

After the liquid is fully incorporated into the $3^{rd}$ diaper a timer built with a waiting time of 5 min The acquisition time is measured.

After 5 min, a new dose entered and the acquisition time is record.

This is repeated twice. A total of 4 doses are added so that 4 acquisition times are obtained.

From about 20 to 30 g of filter papers are weighted. 5 min after the last addition of the fluid, the filter paper is placed on the first diaper. The center of the filter paper must be in line with the center of the diaper and the paper is below the leg cuffs. Weights are added on the plates for 15 seconds (such as acquisition time).

During these 15 seconds a $2^{nd}$ filter paper is placed on the $2^{nd}$ diaper. During the 15 seconds wait for the $2^{nd}$ diaper, the filter paper of the $1^{st}$ diaper is removed and weighed.

The rewet is repeated for the $3^{rd}$ and so on. So as the diapers are measured in pairs.

The rewet (R) is calculated as the weight of the filter after measurement (NW) minus the initial weight of the filter (VW), R=NW−VW Apparatus The product weight is measured at +/−0.1 g, and the filter weights (rewet) is measured +/−0.01 g.

Results

Absorbant structure comprising an unitary absorbent core composed of a nonwoven layer and SAP particles up to 400 g/m$^2$.

| Sample | Type ADL | SAP (g/m$^2$) | Type SAP | Glue (g/m$^2$) | Glue location |
|---|---|---|---|---|---|
| 1 | 15-352 | 400 | FAVOR SXM 10000 | 15 | On the covering layer |
| 2 | 15-395K | 400 | FAVOR SXM 10000 | 12 | On the covering layer |
| 3 | 15-216 | 400 | FAVOR SXM 10000 | 20 | On the covering layer |
| 4 | 15-396 | 400 | FAVOR SXM 10000 | 15 | On the covering layer |
| 5 | 15-216 | 400 | FAVOR SXM 10000 | 5 | On the substrate |

Absorbent structure comprising an ADL and an absorbent core composed of a nonwoven layer and up to 400 g/m$^2$ of SAP particles.

| Sample | Type ADL | SAP (g/m$^2$) | Type SAP | Glue (g/m$^2$) | Glue location |
|---|---|---|---|---|---|
| 6 | 15-352 | 400 | FAVOR SXM 10000 | 15 | glue on covering layer |
| 7 | 15-307 | 400 | FAVOR SXM 10000 | 20 | glue on covering layer |
| 8 | 15-395K | 400 | FAVOR SXM 10000 | 12 | glue on covering layer |
| 9 | 15-396 | 400 | FAVOR SXM 10000 | 15 | glue on covering layer |
| 10 | 15-216 | 400 | FAVOR SXM 10000 | 5 | glue on substrate |

Weight

| | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Wet diaper (g) | 213.255 | 214.507 | 211.243 | 216.78 | 201.273 | 202.003 | 206.23 | 207.47 |
| Dry diaper (g) | 34.1633 | 35.4767 | 31.1567 | 35.7167 | 27.4667 | 27.7967 | 30.5567 | 30.3633 |
| Fluid capacity (g) | 179.0917 | 179.0303 | 180.0863 | 181.0633 | 173.8063 | 174.2063 | 175.6733 | 177.1067 |

From this table it is apparent that for a similar fluid capacity, the sample 9 (glue Bostik and Fuller) with a C fold C-wrap system are the lightest diapers. Making their suitable for comfortable diapers.

Thickness (Mm) at 0.5 kPa

| | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Front | 6.20 | 5.70 | 2.45 | 3.49 | 3.66 | 3.36 | 3.79 | 3.61 |
| Middle | 9.26 | 8.44 | 7.69 | 7.33 | 5.13 | 4.44 | 4.98 | 5.12 |
| Back | 3.42 | 4.17 | 1.17 | 1.13 | 3.52 | 2.91 | 3.58 | 3.63 |

While Dry Max diapers are thin at the front and the back region, their thickness are not homogenous and are particularly thick in the middle section, whereas sample 9 diapers remain thinner throughout the whole diaper length.

Inlet Time

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Inlet time 1 | 44.01 | 67.29 | 26.837 | 27.12 | 49.66 | 46.41 | 47.35 | 45.43 |
| Inlet time 2 | 80.60 | 110.52 | 50.20 | 37.07 | 98.38 | 83.58 | 99.39 | 95.66 |
| Inlet time 3 | 143.52 | 164.35 | 54.50 | 46.95 | 116.36 | 92.66 | 128.66 | 103.71 |

Dry Max diapers provide the fastest inlet time. However samples 9 and 7 materials demonstrate satisfactory inlet time which are similar or better than the Libero samples. From the samples of the invention, Sample 9 Glue fuller C-wrap gives good inlet time, particularly after the $3^{rd}$ inlet.

Rewet

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Rewet 1 | 0.18 | 0.12 | 0.17 | 0.10 | 0.14 | 0.19 | 0.10 | 0.20 |
| Rewet 2 | 0.13 | 0.15 | 0.16 | 0.13 | 0.15 | 0.15 | 0.27 | 0.21 |
| Rewet 3 | 0.14 | 0.17 | 0.16 | 0.13 | 5.9 | 5.50 | 2.78 | 1.92 |

Spreading

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Spreading (cm) | 22.67 | 25.33 | 23.83 | 24.67 | 26.67 | 26.00 | 26.00 | 27.67 |

"Spreading of liquid after the Kanga test is all quite similar."

Spreading

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Spreading (cm) | 20.25 | 21.83 | 25.00 | 26.50 | 25.38 | 24.50 | 21.38 | 26.33 |

Dry Max no 5 obtains excellent spreading. The sample 9 type diapers also demonstrate good spreading ability, comparable to the Dry Max products.

Amount of Absorbed Fluid

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Absorbed fluid (g) | 193.50 | 168.53 | 226.45 | 216.53 | 172.70 | 160.20 | 185.23 | 176.87 |

Absorbed fluid amount is best for Dry Max. Sample 9 Glue Bostik C-wrap, Sample 9 Glue Fuller Envelop wrap and Sample 7 Glue fuller score better than Libero n°5.

Time Before Leakage

|  | Libero n° 4 | Libero n° 5 | Dry Max n° 4 | Dry Max n° 5 | Sample 9 Glue Bostik C-wrap | Sample 9 Glue fuller C-wrap | Sample 9 Glue fuller Envelop wrap | Sample 7 Glue fuller |
|---|---|---|---|---|---|---|---|---|
| Time before leakage_(s) | 1061.23 | 964.13 | 1214.53 | 1174.63 | 963.176 | 894.20 | 1040.73 | 1000.70 |

The times before leakage tested on the samples are excellent, particularly for the Dry Max and the sample 9 glue Fuller envelop wrap and Sample 7 glue Fuller.

From these test it is apparent that sample 9 glue Fuller C-wrap and sample 9 glue Fuller envelop wrap demonstrate excellent overall results.

The invention claimed is:

1. An absorbent article to be applied on a body on a bodyside of the absorbent article, for absorption of body fluids, comprising at least one unitary absorbent structure comprising:
    a non-woven absorbent core comprising a non-woven fibrous substrate having:
        a top layer for liquid acquisition,
        a non-porous intermediate layer having a void volume ranging from about 10 cm$^3$/m$^2$ to about 600 cm$^3$/m$^2$, and
        at least one non-woven fibrous substrate layer having a void volume between 600 cm$^3$/m$^2$ and 6000 cm$^3$/m$^2$ penetrated by super absorbent particles (SAP) in an amount up to 1000 g/m$^2$, said super absorbent particles being dispersed in the non-woven fibrous substrate layer according to a particle size distribution gradient along a depth direction or z-direction of said absorbent core and/or acquisition and dispersion layers, wherein smaller particles are located on the bodyside of the absorbent article and the larger particles are located on an opposite side of the absorbent article,
    a non-porous core-covering layer having a void volume between 10 and 600 cm$^3$, to prevent the release of the SAP outside of the absorbent structure, and
    a liquid impervious backsheet.

2. Absorbent article according to claim 1, wherein said absorbent structure is free of fluff.

3. Absorbent article according to claim 1, wherein said super absorbent particles size dispersion ranges from about 45 µm to about 850 µm.

4. Absorbent article according to claim 1, wherein said substrate layer is a multilayer substrate.

5. Absorbent article according to claim 1, wherein the non-woven fibrous substrate includes fibers selected from the group consisting of polyester or polyethylene terephthalate (PET), polyethylene (PE), polypropylene (PP), coPP, PET/PE, PET/PP, PET/cop, PP/PE, PLA, PLA/PP, PVA, viscose, cotton, wool, PET/coPET, acetate, PTE, PVC, Bamboo, PBT, PA, Acryl, and Modacryl regenerated fibers.

6. Absorbent article according to claim 1, wherein the super absorbent particles are polyacrylate polymers.

7. Absorbent article according to claim 1, wherein the super absorbent particles are deposited depending on a profile along a longitudinal direction or x-direction of said absorbent structure.

8. Absorbent article according to claim 1, wherein the super absorbent particles are deposited depending on a profile along a lateral direction or y-direction of said absorbent structure.

9. Absorbent article according to claim 1, wherein the super absorbent particles are dispersed in discrete zones on the substrate separated from one another, thereby facilitating the flow and wicking of fluid along a longitudinal direction or x-direction and/or a lateral direction or y-direction of said absorbent structure.

10. Absorbent article according to claim 1 comprising an additional acquisition layer and an additional dispersion layer positioned on top of said absorbent structure.

11. Absorbent article according to claim 10 comprising an additional absorbent core positioned underneath said absorbent structure.

12. Absorbent article according to claim 1 comprising at least 2 absorbent structures.

13. Absorbent article according to claim 1 wherein said absorbent article is body shaped.

14. Absorbent article according to claim 1 wherein said absorbent article is selected from the group consisting of a diaper, a light and/or heavy incontinent pad, a feminine care sanitary napkin and a panty liner or a wound dressing.

15. Absorbent article according to claim 14 wherein said absorbent article comprises from about 0.1 to about 1000 g/m$^2$, of super absorbent particles.

\* \* \* \* \*